United States Patent [19]

Bush et al.

[11] Patent Number: 4,663,071

[45] Date of Patent: May 5, 1987

[54] ETHER CARBOXYLATE DETERGENT BUILDERS AND PROCESS FOR THEIR PREPARATION

[75] Inventors: Rodney D. Bush; Daniel S. Connor; Stephen W. Heinzman, all of Cincinnati; Larry N. Mackey, Fairfield, all of Ohio

[73] Assignee: The Procter & Gamble Company, Cincinnati, Ohio

[21] Appl. No.: 823,909

[22] Filed: Jan. 30, 1986

[51] Int. Cl.⁴ .............................................. C11D 17/00
[52] U.S. Cl. .............................. 252/174.19; 252/142; 252/DIG. 11
[58] Field of Search .......... 252/DIG. 11, 142, 174.19; 560/180

[56] References Cited

U.S. PATENT DOCUMENTS

| | | | |
|---|---|---|---|
| Re. 28,325 | 1/1975 | White et al. | 210/58 |
| 3,128,287 | 4/1964 | Berg | 260/346.8 |
| 3,635,830 | 1/1972 | Lamberti et al. | 252/152 |
| 3,692,685 | 9/1972 | Lamberti et al. | 252/89 |
| 3,697,453 | 10/1972 | Tate et al. | 252/546 |
| 3,753,913 | 8/1973 | Jarowenko | 252/89 |
| 3,776,850 | 12/1973 | Pearson et al. | 252/89 |
| 3,784,486 | 1/1974 | Nelson et al. | 252/546 |
| 3,914,297 | 10/1975 | Lamberti et al. | 260/535 P |
| 3,943,165 | 3/1976 | Lamberti | 260/484 P |
| 3,954,858 | 5/1976 | Lamberti et al. | 260/535 P |
| 3,965,169 | 6/1976 | Stahlheber | 260/535 P |
| 3,970,698 | 7/1976 | Lannert | 260/535 P |
| 3,980,578 | 9/1976 | Nelson et al. | 252/180 |
| 3,996,150 | 12/1976 | Lamberti | 252/162 |
| 4,011,264 | 3/1977 | House | 260/535 P |
| 4,017,541 | 4/1977 | Stubbs et al. | 260/535 P |
| 4,021,376 | 5/1977 | Lamberti et al. | 252/542 |
| 4,025,450 | 5/1977 | Lamberti et al. | 252/89 R |
| 4,058,554 | 11/1977 | Gutierrez et al. | 560/180 |
| 4,066,687 | 1/1978 | Nelson et al. | 260/535 P |
| 4,079,016 | 3/1978 | Brahm et al. | 252/99 |
| 4,081,420 | 3/1978 | Lamberti | 260/31.8 R |
| 4,100,188 | 7/1978 | Kao | 260/535 P |
| 4,107,064 | 8/1978 | Nelson et al. | 252/89 R |
| 4,125,485 | 11/1978 | Lannert | 252/174.19 |
| 4,145,558 | 3/1979 | Gutierrez et al. | 560/180 |
| 4,152,515 | 5/1979 | Lamberti et al. | 544/107 |
| 4,182,900 | 1/1980 | Crutchfield et al. | 252/DIG. 11 |
| 4,228,027 | 10/1980 | Lamberti et al. | 252/174.19 |
| 4,260,513 | 4/1981 | Lamberti et al. | 252/174.19 |
| 4,289,753 | 9/1981 | Dyroff et al. | 424/48 |
| 4,382,871 | 5/1983 | Lamberti et al. | 252/174.19 |
| 4,566,984 | 1/1986 | Bush | 252/140 |

FOREIGN PATENT DOCUMENTS

| | | |
|---|---|---|
| 150930 | 8/1985 | European Pat. Off. . |
| 0114420 | 8/1975 | Fed. Rep. of Germany . |
| 49-116024 | 11/1974 | Japan . |
| 51-2708 | 1/1976 | Japan . |
| 1379241 | 1/1975 | United Kingdom . |
| 1392053 | 4/1975 | United Kingdom . |

OTHER PUBLICATIONS

Nieuwenhuizen et al; "Synthesis and Calcium Complexation of Polycarboxylic Acids," Tenside Detergents 22 (1985) 5, pp. 247-251.

Primary Examiner—Paul Lieberman
Assistant Examiner—Willie J. Thompson
Attorney, Agent, or Firm—George W. Allen; Steven J. Goldstein; Jack D. Schaeffer

[57] ABSTRACT

Provided herein are ether carboxylate builder compositions comprising a combination of tartrate monosuccinic acid (or salts thereof) and tartrate disuccinic acid (or salts thereof). Such mixtures can be prepared by reacting water-soluble, mixed maleic acid salts with mixed tartaric acid salts. Both components of the resulting ether carboxylate mixture act as sequestering agents and are useful as detergency builders. Detergent and laundry additive compositions incorporating these ether carboxylates can be prepared without use of detergent builder components containing phosphorus or nitrogen.

20 Claims, 1 Drawing Figure

CALCIUM ELECTRODE RESPONSE AS A FUNCTION OF ADDED BUILDER

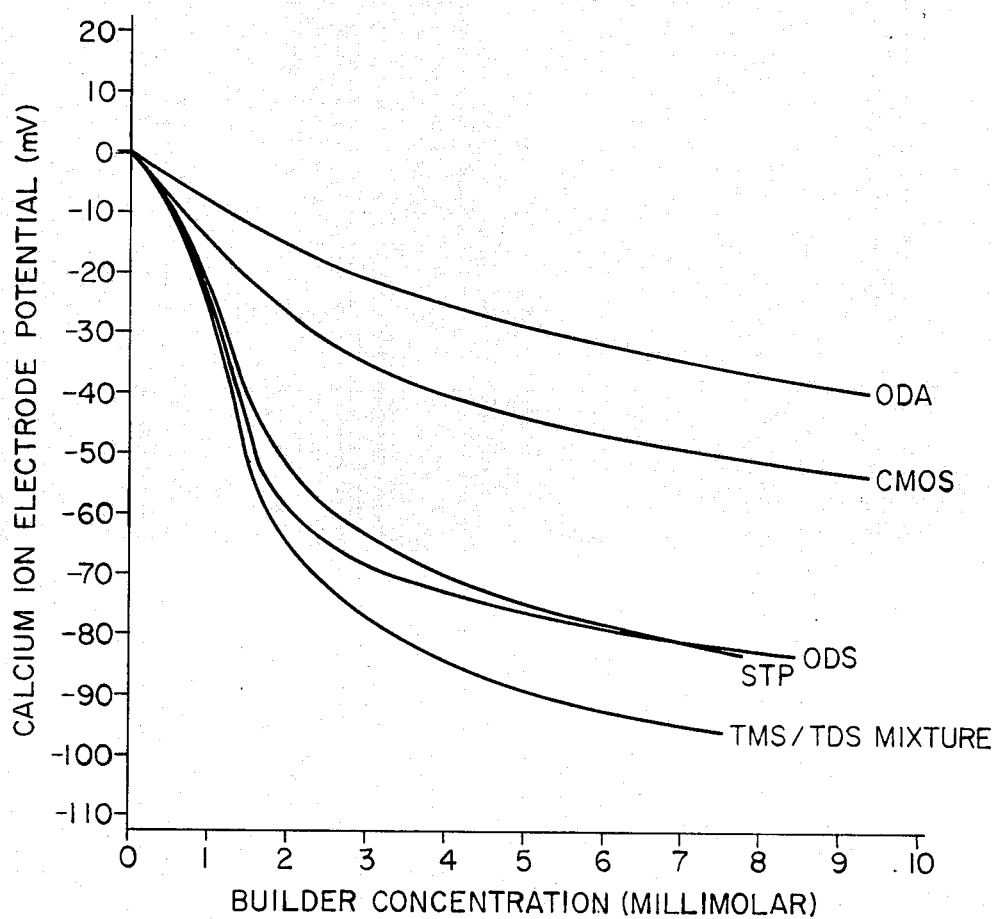

ETHER CARBOXYLATE DETERGENT BUILDERS AND PROCESS FOR THEIR PREPARATION

BACKGROUND OF THE INVENTION

The present invention relates to ether carboxylate-containing compositions and to a process for making them. These ether carboxylate materials are effective sequestering agents and are useful as builders in detergent compositions for household, institutional and industrial use.

The role of sequestering agents in softening water by complexing the "hardness" cations in water supplies is well-known. Sequestering agents are recognized aids in detergent processes because they form a soluble complex with calcium and magnesium ions which can react with soaps and other anionic surfactants and otherwise adversely affect detergency. Polyphosphates such as tripolyphosphates and pyrophosphates are widely used as ingredients in detergent compositions in part because of their property of sequestering hardness ions. Such phosphorus-containing compounds as well as nitrogen-containing compounds, e.g., nitrilotriacetates, are highly effective. However, the effect of the phosphorus content and the nitrogen content of these sequestering agents upon eutrophication of lakes and streams has been questioned, and the use of phosphates in detergent compositions has been subject to government scrutiny, regulation or prohibition.

These circumstances have developed a need for highly effective and efficient phosphorus-free and nitrogen-free sequestering agents and detergency builders. A variety of phosphorus-free and nitrogen-free builder materials have, in fact, been prepared in the form of polycarboxylate compounds. Especially preferred polycarboxylate builders from the standpoint of hardness sequestering capacity and builder performance are the ether polycarboxylates.

A number of types of ether polycarboxylates are known in the art and, along with methods for their preparation, have been disclosed in the patent literature. For example, Stubbs et al; U.S. Pat. No. 4,017,541; Issued Apr. 12, 1977 disclose dicarboxyalkyl ethers of the formula:

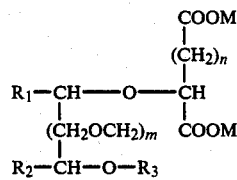

wherein $R_1$ is H,—$CH_3$ or —COOM; $R_2$ is H or COOM; $R_3$ is H,—$CH_2COOM$ or —$CH(COOM)(CH_2)_n$(-COOM), n is 0 or 1, m is 0, 1 or 2 or M is H,—$CH_3$, —$C_2H_5$ or alkali metal. Preferred compounds of this type are said to include propylene glycol monosuccinyl ether and propylene glycol disuccinyl ether.

Pearson et al; U.S. Pat. No. 3,776,850; Issued Dec. 4, 1973 disclose polymeric polycarboxylate builder compounds of the formula:

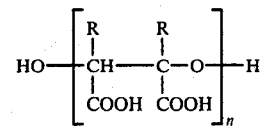

wherein R can be hydrogen and n ranges from 2 to 4. Builder compositions of this type usually contain a mixture of polymers having structures within this general formula.

Berg; U.S. Pat. No. 3,128,287; Issued Apr. 7, 1964 and Lamberti et al; U.S. Pat. No. 3,635,830; Issued Jan. 18, 1972 both disclose oxydisuccinic acid and salts thereof. The '830 patent discloses the use of this oxydisuccinic acid material as a detergent builder.

The disclosed methods for preparing the ether carboxylates of the foregoing patents in general involve the alkaline earth metal catalyzed reaction of carboxylic reactants such as maleic anhydride, maleic acid, and their derivatives. For example, oxydisuccinate builder materials as disclosed in the aforementioned U.S. Pat. Nos. 3,128,287 and 3,635,830 are prepared by heating maleic anhydride or maleic acid in the presence of a molar excess of calcium hydroxide, followed by acid treatment of the resulting reaction product. Such processes employing these particular reactants, however, have especially slow reaction kinetics and furthermore result in relatively low conversions of starting material to the desired ether carboxylate reaction product. These processing disadvantages render such materials as oxydisuccinate less attractive for use as builders in detergent products to be commercially marketed in large volume.

Therefore, notwithstanding the existence of the foregoing types of ether carboxylate detergent builders and ether carboxylate preparation processes, there remains a continuing need to identify additional non-phosphorus, non-nitrogen sequestering agents such as ether carboxylates which can be prepared via commercially acceptable synthesis processes and which can be employed in commercially useful and practical detergent compositions. Accordingly, it is an object of the present invention to provide novel ether carboxylate builder compositions and components thereof, which compositions and components can serve as especially effective builder materials in both granular and liquid detergent and laundry additive compositions.

It is a further object of the present invention to provide a process for preparing ether carboxylate materials of this type via an efficient, high yield reaction which utilizes simple, commercially available reactants.

It is a further object of the present invention to provide detergent compositions and laundry additive compositions employing such novel ether carboxylate compounds as sequestering builders.

SUMMARY OF THE INVENTION

In its composition aspects, the present invention relates to ether carboxylate detergent builder compositions comprising from about 1% to 99% by weight of a tartrate monosuccinic acid, or a salt thereof, and from about 1% to 99% by weight of a tartrate disuccinic acid, or salt thereof. Separate claims to each of these novel builder composition components are also presented. Likewise claims are also presented to detergent compositions and laundry additive compositions containing (1) the ether carboxylate compositions herein or (2) the novel components of such compositions.

In its process aspects, the present invention relates to a process for preparing a mixture of ether carboxylates useful as detergent builder composition. Such process involves the formation of an aqueous reaction mixture containing, as reactants, from about 20% to 60% by weight of both calcium and monovalent cation salts of maleic acid and tartaric acid. Such a reaction mixture corresponds to the over-neutralized mixture which is formed by combining maleic and tartaric acids in a molar ratio of from about 0.5:1 to about 8:1, along with particular amounts of a source of calcium cations and a neutralizing agent comprising an hydroxide of a monovalent cation. The source of calcium cations, preferably calcium hydroxide, is added to the reaction mixture in a molar ratio of calcium to tartaric acid within the range of from about 0.1:1 to 2:1 with the proviso that the moles of calcium added not exceed the total moles of maleic and tartaric acids added. The monovalent cation-containing neutralizing agent is added in an amount such that the ratio of monovalent cations to moles of maleic acid plus moles of tartaric acid minus moles of calcium ranges from about 2.1:1 to about 3.8:1. Such a reaction mixture is maintained at a temperature of from about 20° C. to 120° C. for a period of time sufficient to form a reaction product mixture containing both (a) tartrate monosuccinic acid salt, and (b) tartrate disuccinic acid salt. The resulting reaction product mixture is thereafter treated to reduce its calcium content to the extent that the molar ratio of calcium to the tartrate succinate product compounds therein is less than about 1:10.

BRIEF DESCRIPTION OF THE DRAWING

The drawing provides an illustration of the concentration of free calcium ion in a solution into which solutions of various builder materials, including those of the present invention, are titrated.

DETAILED DESCRIPTION OF THE INVENTION

The principal component of the ether carboxylate builder compositions of the present invention is a particular novel tartrate monosuccinic acid, or salts thereof, having the structural formula:

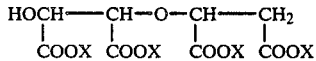

wherein X is H or a salt-forming cation. This tartrate monosuccinic acid or salt thereof is hereinafter designated as "TMS." "TMS" is used to designate both the acid and salt forms of this material.

The tartrate monosuccinic acid component may be employed in the compositions herein in its free acid form, i.e., wherein X in the structural formula is H. Alternatively, and preferably, this material may be partially or fully neutralized to a tartrate monosuccinate salt. Preferred salt-forming cations useful in forming the neutralized materials are those which yield substantially water-soluble salts of tartrate monosuccinic acid. Examples of such preferred salt-forming cations include alkali metal (e.g., sodium, potassium, lithium), ammonium, $C_1$–$C_4$ alkyl substituted ammonium and $C_1$–$C_4$ alkanolamine. The most preferred salt-forming cations are sodium, potassium, monoethanolamine and triethanolamine.

The tartrate monosuccinic component will generally be present in the builder compositions of this invention in an amount ranging from about 1% to 99% by weight of the composition. More preferably, the tartrate monosuccinate component will comprise from about 10% to 98% by weight of the builder compositions herein. Most preferably, this component is present to the extent of from about 20% to 97% by weight of the builder composition.

The second essential component of the ether carboxylate builder compositions of this invention is the particular novel polycarboxylate, tartrate disuccinic acid, or a salt thereof, having the structural formula:

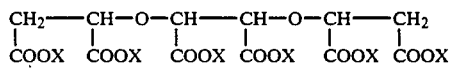

wherein X is H or a salt-forming cation. Tartrate disuccinic acid, or a salt thereof, is hereinafter designated as "TDS."

As with the TMS component, the TDS component can be utilized in either its free acid form or in its partially or fully neutralized form in the builder compositions herein. Neutralizing cations are likewise those which provide TDS in the form of its substantially water-soluble salt. Examples of suitable salt-forming cations include the same cations hereinbefore described for formation of the tartrate monosuccinate material. For convenience both the acid and salt forms of the TDS material will hereinafter be referred to as the "tartrate disuccinate" or "TDS" component.

The TDS component will generally be present in the builder compositions of this invention in an amount ranging from about 1% to 99% by weight of the composition. More preferably, the TDS component will comprise from about 2% to 90% by weight of the builder compositions herein. Most preferably, TDS is present to the extent of from about 3% to 80% by weight.

The builder compositions of the present invention need only contain the tartrate monosuccinate and tartrate disuccinate components hereinbefore described and can be prepared in the form of solid or granular compositions containing these components. Frequently however, the builder compositions herein will contain optional materials such as those used or formed during the preparation of the builder compositions as hereinafter described. Most frequently, one such optional ingredient of the builder compositions herein will be water or moisture from the aqueous reaction mixture used to prepare the builder compositions. Other possible optional ingredients include unreacted reactants such as maleates, tartrates and alkaline earth metals, e.g., calcium, (in ionic, complex, or salt form) used in the preparation of the TMS and TDS components. Likewise, the builder compositions will frequently contain some by-products of the process used for composition preparation. Such by-products can include, for example, malates, maleates, tartrates, fumarates and the like.

No matter what the nature of the optional components, the builder compositions herein will generally contain no more than about 70% by weight of the composition of such optional components. Since the compositions herein are to be used as detergent builders, it is especially important that such compositions contain especially low levels of alkaline earth metals such as calcium. The builder compositions of this invention should generally contain no more than about 10 mole percent of calcium based on the total moles of TMS and TDS present.

Whether or not the builder compositions herein contain significant amounts of optional ingredients, the two essential ether carboxylate components will generally be present in such compositions in a tartrate monosuccinate to tartrate disuccinate weight ratio of from about 97:3 to 20:80. More preferably, this weight ratio will range from about 95:5 to 40:60.

It has been discovered that the particular two-component builder mixtures of the present invention provide hardness, e.g. calcium, sequestering performance which is superior to that of known ether carboxylate builder materials such as carboxymethyloxysuccinate and oxydisuccinate and which is also superior to that of conventional builder materials such as sodium tripolyphosphate. Furthermore it has also been discovered that certain of the two-component builder compositions herein, i.e., those containing the hereinbefore described preferred ratios of TMS to TDS, can be prepared by a procedure hereinafter described with especially high conversion of reactants to desired builder materials after especially short reaction time.

Both the tartrate monosuccinate, i.e., TMS, component and the tartrate disuccinate, i.e., TDS, component of the builder compositions herein can be synthesized by the reaction of mixed calcium and monovalent cation maleic acid salts with mixed calcium and monovalent cation tartaric acid salts. Such a reaction, in fact, produces a mixture of tartrate monosuccinate and tartrate disuccinate with the relative amounts of tartrate monosuccinate and tartrate disuccinate in such a mixture depending on the molar ratio of the maleate and tartrate reactants used and the reaction conditions used. Accordingly, such a reaction can be used to directly form the two-component builder compositions of this invention, and this reaction thus forms the basis of the builder composition preparation process of the present invention.

The first step of the builder composition preparation process herein involves the formation of an aqueous reaction mixture containing particular amounts of a maleate reactant comprising both monovalent cation and calcium salts of maleic acid and a tartrate reactant comprising both monovalent cation and calcium salts of tartaric acid. The total amount of maleate plus tartrate reactants in the reaction mixture will generally range from about 20% to 60% by weight of the mixture, more preferably from about 40% to 55% by weight. Materials which yield these reactants in solution can be dissolved in water to form the reaction mixture used in this process.

Usually both the maleate and tartrate reactants in requisite mixed salt form and amounts can be generated in the reaction mixture in situ. This can be done by combining in aqueous solution certain amounts of maleic acid or maleic anhydride, tartaric acid, a source of calcium cations and, as a neutralizing agent, an hydroxide of a monovalent cation in certain amounts. The molar ratio of maleic acid to tartaric acid in such solutions will generally range from about 0.5:1 to 8:1, more preferably from about 0.9:1 to 1.2:1. The ratio of maleic and tartaric acids which is used will depend upon the relative amounts of tartrate monosuccinate and tartrate disuccinate desired in the builder composition to be prepared.

A source of calcium cations, which act as a catalyst for the tartrate succinate-forming reaction, is generally added to such aqueous solutions in an amount such that the ratio of calcium cations to tartaric acid range from about 0.1:1 to about 2.0:1, more preferably from about 0.8:1 to 1.5:1. However, within this ratio range, the amount of calcium added should be such that the ratio of moles of calcium cations to total moles of maleic and tartaric acids in solution is less than 1. Any compound which yields calcium cations in solution can be employed as the calcium cation source. Such compounds include calcium hydroxide and water-soluble calcium salts. Calcium hydroxide is highly preferred since it acts as both a calcium cation source and a neutralizing agent.

An hydroxide of a monovalent cation is also essentially added to the reactant mixture as a neutralizing agent. This neutralizing agent is usually added in an amount such that the ratio of moles of monovalent cations to total moles of tartaric acid plus the moles of maleic acid minus the moles of calcium cations ranges from about 2.1:1 to about 3.8:1. More preferably this ratio ranges from about 2.2:1 to about 3:1. The monovalent cation-containing neutralizing agent can be any hydroxide which upon addition to water yields monovalent neutralizing cations in solution. Such neutralizing agents include, for example, alkali metal, ammonium or substituted ammonium hydroxide. Sodium hydroxide is highly preferred.

Enough neutralizing base (e.g. calcium hydroxide and monovalent cation hydroxide) should be added to the reaction mixture to ensure that the reaction mixture is over-neutralized. Thus the reaction mixtures of this invention will generally have a pH within the range of from about 8.5 to 13, more preferably from about 9.5 to 12.5.

In forming the reaction mixture of the present process, it is possible to employ precursors of the essential reaction mixture components. Precursors of the tartrate and maleate mixed salt reactants in solution can take a variety of forms. For example, tartaric acid in either its D-, L- or DL-stereoisomer form is suitable for use as the precursor of the tartrate reactant. It is also possible to generate tartaric acid in situ by reaction of maleic acid and hydrogen peroxide using, for example, a tungstate catalyst. The maleate reactant can be derived from maleic acid. Maleic acid itself can be formed in aqueous solution by the addition of maleic anhydride to water.

It is, of course, also possible to form the reaction mixture used in the process herein by adding the tartrate and maleate reactants in their appropriate salt forms to water and to thereby prepare the reaction mixture without the step of in situ neutralization. If the reaction mixture is formed in this manner, amounts of the tartrate, maleate and calcium materials, as well as added neutralizing agents, should be selected so that the resulting solution corresponds in composition to the hereinbefore described reaction mixtures formed by in situ generation of the essential reaction mixture components.

As indicated hereinbefore, the preferred process of the present invention employing reactant molar ratios of maleate to tartrate within the range of 0.9:1 to 1.2:1 is especially advantageous from the reactant conversion and reaction kinetics standpoint. At reactant ratios within this range, total reactant conversion levels as high as 84% can be realized in comparison with the much lower conversion percentages reported for preparation of such materials as oxydisuccinate using a maleic anhydride reactant. Without being bound by theory, the improved conversion percentages which can be realized using the preferred process embodiments of the present invention may be in part due to the inherently greater stability of TMS in the reaction mixture in comparison with oxydisuccinate (ODS) under similar conditions. TMS under conditions used for its formation does not appear to decompose as readily as oxydisuccinate to unreactive by-products such as fumarate, thereby enhancing both TMS formation and subsequent TDS formation from TMS. It should also be noted that irrespective of conversion percentage, production of MHODS/TDS mixtures in general can be realized in a relatively short reaction time compared with the extended reaction times which are reported to be required for preparation of other ether carboxylates such as oxydisuccinate.

It should also be noted that use of the hereinbefore described particular amounts of the calcium cation source is likewise believed to play a role in realizing the improved conversion levels achieved with the process of the present invention. In direct contrast to prior art teaching regarding ether carboxylate preparation (See, for example, U.S. Pat. No. 3,635,830), the amount of calcium in the reaction mixture of the present process should be kept within the hereinbefore described concentration limits in order to avoid formation of a large amount of insoluble or sparingly soluble calcium salts of the maleate and tartrate reactants. Utilization of these reactants in their soluble, mixed salt, e.g. sodium/calcium, form may facilitate the kinetics of the ether carboxylate-forming reaction and accordingly improve product yield.

After the aqueous reaction mixture hereinbefore described has been formed by combining the separate reactants and catalyst, or precursors thereof, in the required concentrations, the builder composition forming reaction is carried out by maintaining the aqueous reaction mixture at a temperature of from about 20° C. to 120° C., preferably from about 50° C. to 80° C., for a period of time sufficient to form a reaction product mixture which contains the desired amounts of the tartrate monosuccinate and tartrate disuccinate components of the compositions herein. Reaction times of from about 0.5 to 10 hours, more preferably from about 1 to 4 hours will generally be suitable for realizing acceptable yields of the two essential components of the builder compositions herein.

After the ether carboxylate forming reaction has been completed to the desired extent, the calcium content of the aqueous reaction must be reduced. Removal of calcium to effect this reduction can be carried out in a number of ways known in the art. Frequently, calcium can be removed from the product mixture by adding thereto a calcium precipitating material having a greater affinity for reaction with calcium than do the tartrate monosuccinate and tartrate disuccinate reaction products. Such materials can include, for example, precipitating chelating agents such as ethanehydroxydiphosphonic acid, or salts thereof, (EHDP) or calcium precipitating materials such as alkali metal carbonate, pyrophosphate, bicarbonate and/or alkali metal silicate. The resulting calcium precipitate can thereafter be removed from the aqueous reaction product mixture by filtration. An alternate means for removing calcium from the aqueous reaction product mixture involves treatment of the reaction product mixture with an appropriate innsoluble ion exchange resin. No matter what technique is employed, calcium content of the aqueous reaction mixture should be reduced to the extent that the ratio of moles of calcium to total moles of tartrate monosuccinate and tartrate disuccinate is less than about 1:10, preferably less than about 1:20.

Preferably in addition to such calcium reduction processing, the reaction product mixture of the present invention may also optionally be treated to remove excess reactants of reaction by-products such as maleates, malates, tartrates and fumarates. This can be accomplished by conventional salt separation procedures using a solvent such as methanol in which these excess reactants and reaction by-products are relatively soluble and in which the desired tartrate monosuccinate and tartrate disuccinate are relatively insoluble.

After the calcium content of the aqueous reaction product mixture has been reduced to the requisite levels, and, if desired, after excess reactants and reaction by-products have been removed, the reaction product mixture may be concentrated by a removal of water to the desired extent. Water removal may, for example, involve substantially complete drying of the reaction product mixture, e.g., by spray drying, so that the ether carboxylate builder mixture is recovered in solid, e.g., granular, form. Alternatively, the builder composition in the form of an aqueous liquid may be utilized directly in the preparation of detergent compositions or laundry additive products of the types more fully described hereinafter.

After reduction of the calcium content in the reaction product mixture, it is possible, if desired, to acidify the product mixture using conventional acidification or ion exchange techniques to convert the ether carboxylate products therein to their free acid form. Normally, however, the tartrate monosuccinate and tartrate disuccinate materials of this invention can be used as builders in their water-soluble salt form, and such acidification is therefore not usually necessary or desirable.

It is also possible, if desired, to separate the individual components of the resulting builder mixture and recover such compounds as substantially pure TMS and TDS materials. Such component separation can be effected, for example, using conventional liquid chromatographic techniques. For use in some types of detergent compositions, it may be desirable to use either TMS or TDS as substantially pure materials. More frequently, however, recovery of the individual TMS and TDS components as substantially pure materials is neither necessary nor particularly advantageous.

The ether carboxylate builder compositions herein, or the individual tartrate monosuccinate and tartrate disuccinate components thereof, may be employed as sequestering builders in a wide variety of detergent compositions or laundry additive compositions. These particular builder materials are believed to be especially effective in promoting certain types of fabric cleaning in comparison with a number of structurally similar carboxylate builders of the prior art. Such materials also retain their efficacy as detergent builders even in relatively low pH cleaning solutions. The specific ether carboxylate materials of this invention furthermore possess especially desirable biodegradability characteristics.

Detergent compositions incorporating the ether carboxylate materials of the present invention contain as essential components from about 0.5% to about 98% of a surfactant and from about 2% to about 99.5% of the ether carboxylate compounds or mixtures of the present invention as a detergency builder.

Typical laundry detergent compositions within the scope of the present invention contain from about 5% to about 30% of a surfactant and from about 5% to about 80% total detergency builder. Of this builder component from about 20% to 100% by weight of builder component can be the ether carboxylate compounds or mixtures of the present invention with the balance of the builder component being optional known builders.

Detergent compositions herein may also contain from about 5% to 95% by weight of a wide variety of additional optional components. Such optional components can include, for example, additional detergent builders, chelating agents, enzymes, fabric whiteners and brighteners, sudsing control agents, solvents, hydrotropes, bleaching agents, bleach precursors, buffering agents, soil removal/anti-redeposition agents, soil release agents, fabric softening agents, perfumes, colorants and opacifiers. A number of these additional optional components are hereinafter described in greater detail.

The detergent compositions of this invention are effective in cleaning solutions over the broad cleaning solution pH range of from about 6 to about 13. The compositions can be formulated to provide a desired cleaning solution pH by proper selection of the acid form of appropriate salts or mixtures thereof. Preferred water-soluble salts of the builder compounds, for example, can be the alkali metal salts such as sodium, potassium, lithium and ammonium or substituted ammonium, e.g. triethanol ammonium. Depending on the pH of the desired solution, the salts are partially or full neutralized.

The detergent compositions of this invention can be prepared in solid or liquid physical form.

The detergent compositions of this invention are particularly suitable for laundry use, but are also suitable for the cleaning of hard surfaces and for dishwashing.

In a laundry method using the detergent composition of this invention, typical laundry wash water solutions comprise from about 0.1% to about 1% by weight of the detergent compositions of this invention.

The ether carboxylate materials herein may also be employed as builders in laundry additive compositions. Laundry additive compositions of the present invention contain as essential components from about 2% to about 99.5% of the ether carboxylate compounds or mixtures of the present invention and further contains from about 0.5% to 98% by weight of a laundry adjuvant selected from the group consisting of surfactants, alternate builders, enzymes, fabric whiteners and brighteners, sudsing control agents, solvents, hydrotropes, bleaching agents, bleach precursors, buffering agents, soil removal/antideposition agents, soil release agents, fabric softening agents, perfumes, colorants, opacifiers and mixtures of these adjuvants. Such adjuvants, whether used in the detergent or laundry additive compositions herein, perform their expected functions in such compositions. A number of these adjuvants are described in greater detail as follows:

Surfactants

Various types of surfactants can be used in the detergent or laundry additive compositions of this invention. Useful surfactants include anionic, nonionic, ampholytic, zwitterionic and cationic surfactants or mixtures of such materials. Detergent compositions for laundry use typically contain from about 5% to about 30% anionic surfactants, mixtures of anionic and nonionic surfactants or cationic surfactants. Detergent compositions for use in automatic dishwashing machines typically contain from about 2% to about 6% by weight of a relatively low sudsing nonionic surfactant or mixtures thereof and, optionally, suds control agents. Particularly suitable low sudsing nonionic surfactants are the alkoxylation products of compounds containing at least one reactive hydrogen wherein, preferably, at least about 20% by weight of the alkylene oxide by weight is propylene oxide. Examples are products of the BASF-Wyandotte Corporation designated Pluronic ®, Tetronic ®, Pluradot ® and block polymeric variations in which propoxylation follows ethoxylation. Preferred suds control agents include mono- and distearyl acid phosphates.

The various classes of surfactants useful in the detergent and laundry additive compositions herein are exemplified as follows:

(A) Anionic soap and non-soap surfactants

This class of surfactants includes alkali metal monocarboxylates (soaps) such as the sodium, potassium, ammonium and alkylolammonium salts of higher fatty acids containing from about 8 to about 24 carbon atoms and preferably from about 12 to about 18 carbon atoms. Suitable fatty acids can be obtained from natural sources such as, for instance, from plant or animal esters (e.g., palm oil, coconut oil, babassu oil, soybean oil, castor oil, tallow, whale and fish oils, grease, lard, and mixtures thereof). The fatty acids also can be synthetically prepared (e.g., by the oxidation of petroleum, or by hydrogenation of carbon monoxide by the Fischer-Tropsch process). Resin acids are suitable such as rosin and those resin acids in tall oil. Naphthenic acids are also suitable. Sodium and potassium soaps can be made by direct saponification of the fats and oils or by the neutralization of the free fatty acids which are prepared in a separate manufacturing process. Particularly useful are the sodium and potassium salts of the mixtures of fatty acids derived from coconut oil and tallow, i.e., sodium or potassium tallow and coconut soap. Soaps and fatty acids also act as detergency builders in detergent compositions because they remove multivalent ions by precipitation.

Anionic surfactants also include water-soluble salts, particularly the alkali metal and ethanolamine salts of organic sulfuric reaction products having in their molecular structure an alkyl radical containing from about 8 to about 22 carbon atoms and a sulfonic acid or sulfuric acid ester radical. (Included in the term alkyl is the alkyl portion of alkylaryl radicals.) Examples of this group of non-soap anionic surfactants are the alkyl sulfates, especially those obtained by sulfating the higher alcohols ($C_8$–$C_{18}$ carbon atoms); alkyl benzene sulfonates, in which the alkyl group contains from about 9 to about 15 carbon atoms, in straight chain or branched chain configuration, sodium alkyl glyceryl ether sulfonates; fatty acid monoglyceride sulfonates and sulfates; sulfuric acid esters of the reaction product of one mole of a $C_{12\text{-}18}$ alcohol and about 1 to 6 moles of ethylene oxide and salts of alkyl phenol ethylene oxide ether sulfate with about 1 to about 10 units of ethylene oxide per molecule and in which the alkyl radicals contain about 8 to about 12 carbon atoms.

Additional examples of non-soap anionic surfactants are the reaction products of fatty acids esterified with isethionic acid and neutralized with sodium hydroxide where, for example, the fatty acids are derived from coconut oil and sodium or potassium salts of fatty acid amide of methyl lauride in which the fatty acids, for example are derived from coconut oil.

Still other anionic surfactants include the class designated as succinamates. This class includes such surface active agents as disodium N-octadecylsulfosuccinamate; tetrasodium N-(1,2-dicarboxyethyl)-N-octadecylsulfosuccinamate; the diamyl ester of sodium sulfosuccinic acid; the dihexyl ester of sodium sulfosuccinic acid and the dioctyl ester of sodium sulfosuccinic acid.

Anionic phosphate surfactants are also useful in the detergent or laundry additive compositions of the present invention. These are surface active materials having substantial detergent capability in which the anionic solubilizing group connecting hydrophobic moieties is an oxy acid of phosphorus. The more common solubilizing groups are $-SO_4H$, $-SO_3H$, and $-CO_2H$. Alkyl phosphate esters such as $(R-O)_2PO_2H$ and $ROPO_3H_2$ in which R represents an alkyl chain containing from about 8 to about 20 carbon atoms are useful.

These esters can be modified by including in the molecule from one to about 40 alkylene oxide units, e.g., ethylene oxide units.

Particularly useful anionic surfactants for incorporation into the compositions herein are alkyl ether sulfates. The alkyl ether sulfates are condensation products of ethylene oxide and monohydric alcohols having about 10 to about 20 carbon atoms. Preferably, R has 12 to 18 carbon atoms. The alcohols can be derived from fats, e.g., coconut oil or tallow, or can be synthetic. Such alcohols are reacted with 0.5 to 30, and especially 1 to 6, molar proportions of ethylene oxide and the resulting mixture of molecular species, having, for example, an average of 3 to 6 moles of ethylene oxide per mole of alcohol, is sulfated and neutralized.

Other suitable anionic surfactants are olefin and paraffin sulfonates having from about 12 to about 24 carbon atoms.

(B) Nonionic surfactants

Alkoxylated nonionic surfactants may be broadly defined as compounds produced by the condensation of alkylene oxide groups (hydrophilic in nature) with an organic hydrophobic compound, which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

Alkoxylated nonionic surfactants include:
(1) The condensation product of aliphatic alcohols having from 8 to 22 carbon atoms, in either straight chain or branched chain configuration, with from about 5 to about 20 moles of ethylene oxide per mole of alcohol.
(2) The polyethylene oxide condensates of alkyl phenols, e.g., the condensation products of alkyl phenols having an alkyl group containing from about 6 to 12 carbon atoms in either a straight chain or branched chain configuration, with ethylene oxide, the ethylene oxide being present in amounts of from about 5 to about 25 moles of ethylene oxide per mole of alkyl phenol. The alkyl substituent in such compounds may be derived from polymerized propylene, diisobutylene, octene, or nonene, for example.
(3) Materials derived from the condensation of ethylene oxide with a product resulting from the reaction of propylene oxide and a compound with reactive hydrogen such as glycols and amines such as, for example, compounds containing from about 40% to about 80% polyoxyethylene by weight resulting from the reaction of ethylene oxide with a hydrophobic base constituted of the reaction product of ethylene diamine and propylene oxide.

Non-polar nonionic surfactants include the amine oxides and corresponding phosphine oxides. Useful amine oxide surfactants include those having the formula $R^1R^2R^3N\rightarrow O$ wherein $R^1$ is an alkyl group containing from about 10 to about 28 carbon atoms, from 0 to about 2 hydroxy groups and from 0 to about 5 ether linkages, there being at least one moiety of $R^1$ which is an alkyl group containing from about 10 to about 18 carbon atoms and $R^2$ and $R^3$ are selected from the group consisting of alkyl radicals and hydroxyalkyl radicals containing from 1 to about 3 carbon atoms.

Specific examples of amine oxide surfactants include: dimethyldodecylamine oxide, dimethyltetradecylamine oxide, ethylmethyltetradecylamine oxide, cetyldimethylamine oxide, diethyltetradecylamine oxide, dipropyldodecylamine oxide bis-(2-hydroxyethyl)-dodecylamine oxide, bis-(2-hydroxypropyl)methyltetradecylamine oxide, dimethyl-(2-hydroxydodecyl)amine oxide, and the corresponding decyl, hexadecyl and octadecyl homologs of the above compounds.

Additional operable nonionic surfactants include alkyl glucosides and alkylamides of the formula

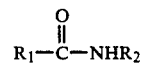

wherein $R_1$ is $C_{10}-C_{18}$ alkyl and $R_2$ is $-H$, $-C_2$ or $-C_2H_5$.

(C) Zwitterionic Surfactants

Zwitterionic surfactants include derivatives of aliphatic quaternary ammonium, phosphonium, and sulfonium compounds in which the aliphatic moiety can be straight or branched chain and wherein one of the aliphatic substituents contains from about 8 to 24 carbon atoms and one contains an anionic water-solubilizing group. Particularly preferred zwitterionic materials are the ethoxylated ammonium sulfonates and sulfates disclosed in U.S. Pat. Nos. 3,925,262, Laughlin et al, issued Dec. 9, 1975 and 3,929,678, Laughlin et al, issued Dec. 30, 1975, said patents being incorporated herein by reference. Ammonioamidates are also useful zwitterionic surfactants.

(D) Ampholytic Surfactants

Ampholytic surfactants include derivatives of aliphatic-heterocyclic seconday and tertiary amines in which the aliphatic moiety can be straight chain or branched and wherein one of the aliphatic substituents contains from about 8 to about 24 carbon atoms and at least one aliphatic substituent contains an anionic water-solubilizing group.

(E) Cationic Surfactants

Cationic surfactants comprise a wide variety of compounds characterized by one or more organic hydrophobic groups in the cation and generally by a quaternary nitrogen associated with an acid radical. Pentavalent nitrogen ring compounds are also considered quaternary nitrogen compounds. Suitable anions are halides, methyl sulfate and hydroxide. Tertiary amines can have characteristics similar to cationic surfactants at washing solutions pH values less than about 8.5.

A more complete disclosure of cationic surfactants can be found in U.S. Pat. No. 4,228,044, issued Oct. 14, 1980, to Cambre, incorporated herein by reference.

When cationic surfactants are used in combination with anionic surfactants and certain detergency builders including polycarboxylates, compatibility must be considered. A type of cationic surfactant generally compatible with anionic surfactants and polycarboxylates is a $C_{8-18}$ alkyl tri $C_{1-3}$ alkyl ammonium chloride or methyl sulfate.

More complete disclosures of surfactants suitable for incorporation in detergent and laundry additive compositions of the present invention are in U.S. Pat. Nos. 4,056,481, Tate (Nov. 1, 1977); 4,049,586, Collier (Sept. 20, 1977); 4,040,988, Vincent et al (Aug. 9, 1977); 4,035,257, Cherney (July 12, 1977); 4,033,718, Holcolm et al (July 5, 1977); 4,019,999, Ohren et al (Apr. 26, 1977); 4,019,998, Vincent et al (Apr. 26, 1977); and 3,985,669, Krummel et al (Oct. 12, 1976); all of said patents being incorporated herein by reference.

Optional Detergency Builders

The detergent and laundry additive compositions of the present invention can contain detergency builders in addition to the ether carboxylate compounds or mixtures described hereinbefore as essential components.

Suitable additional polycarboxylate detergency builders include the acid form and alkali metal, ammonium and substituted ammonium salts of citric, ascorbic, phytic, mellitic, benzene pentacarboxylic, oxydiacetic, carboxymethyloxysuccinic, carboxymethyloxymalonic, cis-cyclohexanehexacarboxylic, cis-cyclopentanetetracarboxylic and oxydisuccinic acids. Also suitable are polycarboxylate polymers and copolymers described in U.S. Pat. No. 3,308,067, Diehl, issued Mar. 7, 1967, incorporated herein by reference. Particularly suitable are acrylic acid polymers and salts thereof and copolymers of acrylic and maleic acids and salts thereof which act as dispersants of particulate materials in wash solutions.

The polyacetal carboxylates disclosed in U.S. Pat. No. 4,144,226 issued Mar. 13, 1979, to Crutchfield et al and U.S. Pat. No. 4,146,495 issued Mar. 27, 1979 to Crutchfield et al can be incorporated in the detergent and laundry additive compositions of the invention.

Also suitable in the detergent and laundry additive compositions of the invention are the 3,3-dicarboxy-4-oxa-1,6-hexanedioates and the related compounds disclosed in U.S. Pat. No. 4566984 issued Jan. 28, 1986, and incorporated herein by reference.

Suitable ether polycarboxylates also include cyclic compounds, particularly alicyclic compounds, such as described in U.S. Pat. Nos. 3,923,679; 3,835,163; 4,158,635; 4,120,874 and 4,102,903, incorporated herein by reference.

Polyphosphonate detergency builders comprise a large range of organic compounds having two or more

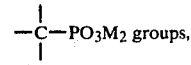

wherein M is hydrogen or a salt-forming radical. Suitable phosphonates include ethane-1-hydroxy-1,1-diphosphonates, ethanehydroxy-1,1,2-triphosphonates and their oligomeric ester chain condensates. Suitable polyphosphonates for use in the compositions of the invention also include nitrogen-containing polyphosphonates such as ethylenediaminetetrakis (methylenephosphonic) acid and diethylenetriaminepentakis (methylenephosphonic) acid and alkali metal, ammonium and substituted ammonium salts thereof. In common with other phosphorus-containing components, the incorporation of phosphonates may be restricted or prohibited by government regulation.

As discussed hereinbefore $C_{8-24}$ alkyl monocarboxylic acid and soluble salts thereof have a detergent builder function in addition to surfactant characteristics. $C_8-C_{24}$ alkyl, alkenyl, alkoxy and thio-substituted alkyl dicarboxylic acid compounds, such as 4-pentadecene -1,2-dicarboxylic acid, salts thereof and mixtures thereof, are also useful optional detergency builders.

Inorganic detergency builders useful in the detergent and laundry additive compositions of this invention at total combined levels of from 0% to about 75% by weight, include alkali metal phosphates, sodium aluminosilicates, alkali metal silicates and alkali metal carbonates.

Phosphate detergency builders include alkali metal orthophosphates which remove multivalent metal cations from laundry solutions by precipitation and the polyphosphates such as pyrophosphates, tripolyphosphates and water-soluble metaphosphates that sequester multivalent metal cations in the form of soluble complex salts or insoluble precipitating complexes. Sodium pyrophosphate and sodium tripolyphosphate are particularly suitable in granular detergent and laundry additive compositions to the extent that governmental regulations do not restrict or prohibit the use of phosphorus-containing compounds in such compositions. Granular detergent and laundry additive composition embodiments of the invention particularly adapted for use in areas where the incorporation of phoshorus-containing compounds is restricted contains low total phosphorus and, preferably, essentially no phosphorus.

Other optional builder material include aluminosilicate ion exchange materials, e.g. zeolites. Crystalline aluminosilicate ion exchange materials useful in the presence of this invention have the formula $Na_z[(AlO_2)_z(SiO_2)_y]H_2O$ wherein z and y are at least about 6, the molar ratio of z to y is from about 1.0 to about 0.5 and x is from about 10 to about 264. In a preferred embodiment the aluminosilicate ion exchange material has the formula $Na_{12}[(AlO_2)_{12}(SiO_2)_{12}]xH_2O$ wherein x is from about 20 to about 30, especially about 27.

Amorphous hydrated aluminosilicate material useful herein has the empirical formula: $Na_z(zAlO_2 \cdot ySiO_2)$, z is from about 0.5 to about 2, y is 1 and said material has a magnesium ion exchange capacity of at least about 50 milligram equivalents of $CaCO_3$ hardness per gram of anhydrous aluminosilicate.

The aluminosilicate ion exchange builder material herein are in hydrated form and contain from about 10% to about 28% of water by weight if crystalline and potentially even higher amounts of water if amorphous. Highly preferred crystalline aluminosilicate ion exchange materials contain from about 18% to about 22% water in their crystal matrix. The crystalline aluminosilicate ion exchange materials are further characterized by a particle size diameter of from about 0.1 micron to about 10 microns. Amorphous materials are often smaller, e.g., down to less than about 0.01 micron. Preferred ion exchange materials have a particle size diameter of from about 0.2 micron to about 4 microns. The term "particle size diameter" herein represents the average particle size diameter of a given ion exchange material as determined by conventional analytical techniques such as, for example, microscopic determination utilizing a scanning electron microscope. The crystalline aluminosilicate ion exchange materials herein are usually further characterized by their calcium ion exchange capacity, which is at least about 200 mg. equivalent of $CaCO_3$ water hardness/gm. of aluminosilicate, calculated on an anhydrous basis, and which generally is in the range of from about 300 mg.eq./g. to about 352 mg. eq./g. The aluminosilicate ion exchange materials herein are still further characterized by their calcium ion exchange rate which is at least about 2 grains $Ca++$/gallon/ minute/gram of aluminosilicate (anhydrous basis), and generally lies within the range of from about 2 grains/gallon/ minute/gram to about 6 grains/gallon/minute/gram, based on calcium ion hardness. Optimum aluminosilicate for builder purposes exhibit a calcium ion exchange rate of at least about 4 grains/gallon/minute/gram.

The amorphous aluminosilicate ion exchange materials usually have a $Mg++$ exchange capacity of at least about 50 mg. eq. $CaCO_3$/g(12 mg. $Mg++$/g.) and a $Mg++$ exchange rate of at least about 1 gr./gal./min./g./gal. Amorphous materials do not exhibit an observable diffraction pattern when examined by Cu radiation (1.54 Angstrom Units).

Aluminosilicate ion exchange materials useful as optional builders in the detergent and laundry additive compositions of this invention are commercially available. The aluminosilicates useful in this invention can be crystalline or amorphous in structure and can be naturally-occurring aluminosilicates or synthetically derived. A method for producing aluminosilicate ion exchange materials is discussed in U.S. Pat. No. 3,985,669, issued Oct. 12, 1976, incorporated herein by reference. Preferred synthetic crystalline aluminosilicate ion exchange materials useful herein are available under the designation Zeolite A, Zeolite B, and Zeolite X.

Other optional builders include alkali metal silicates. Suitable alkali metal silicates have a mole ratio of $SiO_2$:alkali metal oxide in the range of from about 1:1 to about 4:1. The alkali metal silicate suitable herein include commercial preparations of the combination of silicon dioxide and alkali metal oxide or carbonate fused together in varying proportions according to, for example, the following reaction:

The value of m, designating the molar ratio of $SiO_2$:$Na_2O$, ranges from about 0.5 to about 4 depending on the proposed use of the sodium silicate. The term "alkali metal silicate" as used herein refers to silicate solids with any ratio of $SiO_2$ to alkali metal oxide. Silicate solids normally possess a high alkalinity content; in addition water of hydration is frequently present as, for example, in metasilicates which can exist having 5, 6, or 9 molecules of water. Sodium silicate solids with a $SiO_2$:$Na_2O$ mole ratio of from about 1.5 to about 3.5, are preferred in granular laundry detergent compositions.

Silicate solids are frequently added to granular detergent or laundry additive compositions as corrosion inhibitors to provide protection to the metal parts of the washing machine in which the detergent or laundry additive composition is utilized. Silicates have also been used to provide a degree of crispness and pourability to detergent or laundry additive granules which is very desirable to avoid lumping and caking.

Alkali metal carbonates are useful in the granular detergent or laundry additive compositions of the invention as a source of washing solution alkalinity and because of the ability of the carbonate ion to remove calcium and magnesium ions from washing solutions by precipitation.

Preferred granular compositions free of inorganic phosphates contain from about 8% to about 40% by weight sodium carbonate, from 0% to about 30% sodium aluminosilicate, from about 0.5% to about 10% sodium silicate solids, from about 5% to about 35% of the novel ether carboxylate compounds of this invention and from about 10% to about 25% surfactant.

Preferred liquid compositions free of inorganic phosphates contain from about 8% to about 30% by weight of non-soap anionic surfactants, from about 2% to about 25% ethoxylated nonionic surfactants, from about 5% to about 20% of a $C_{8-24}$ alkyl or alkenyl mono-or dicarboxylic acid or salt thereof and from about 2% to about 18% of the novel ether carboxylate compounds of the present invention. Some liquid formulations may also contain from about 0.5 to about 5% of a cationic or amine oxide surfactant.

Additional Optional Components

Granular detergent or laundry additive compositions of this invention can contain materials such as sulfates, borates, perborates organic peroxy acid salts, peroxy bleach precursors and activators and water of hydration.

Liquid detergent or laundry additive compositions of this invention can contain water and other solvents. Low molecular weight primary or secondary alcohol exemplified by methanol, ethanol, propanol, and isopropanol are suitable. Monohydric alcohols are preferred for solubilizing the surfactant but polyols containing from 2 to about 6 carbon atoms and from 2 to about 6 hydroxy groups can be used and can provide improved enzyme stability. Examples of polyols include propylene glycol, ethylene glycol, glycerine and 1,2-propanediol. Ethanol is a particularly preferred alcohol.

The detergent or laundry additive compositions of the invention can also contain such materials as proteolytic and amylolytic enzymes, fabric whiteners and optical brighteners, sudsing control agents, hydrotropes such as sodium toluene, xylene or cumene sulfonate, perfumes, colorants, opacifiers, anti-redeposition agents and alkalinity control or buffering agents such as monoethanolamine and triethanolamine. The use of these materials is known in the detergent art.

Materials that provide clay soil removal/anti-redeposition benefits can also be incorporated in the detergent and laundry additive compositions of the invention and are particularly useful in liquid compositions of the invention. These clay soil removal/anti-redeposition agents are usually included at levels of from about 0.1% to about 10% by weight of the composition.

One group of preferred clay soil removal/anti-redeposition agents are the ethoxylated amines disclosed in European Patent Application No. 112,593 of James M. Vander Meer, published July 4, 1984, incorporated herein by reference. Another group of preferred clay soil removal/anti-redeposition agents are the cationic compounds disclosed in European Patent Application 111,965 to Young S. Oh and Eugene P. Gosselink, published June 27, 1984, incorporated herein by reference. Other clay soil removal/anti-redeposition agents which can be used include the ethoxylated amine polymers disclosed in European Patent Application No. 111,984 to Eugene P. Gosselink, published June 27, 1984; the zwitterionic compounds disclosed in European Patent Application No. 111,976 to Donn N. Rubingh and Eugene P. Gosselink, published June 27, 1984; the zwitterionic polymers disclosed in European Patent Application No. 112,592 to Eugene P. Gosselink, published July 4, 1984; and the amine oxides disclosed in U.S. Pat. No. 4548744 issued Nov. 22, 1985 to Daniel S. Connor, all of which are incorporated herein by reference. Polyethylene glycol can also be incorporated to provide anti-redeposition and other benefits.

Soil release agents, such as disclosed in the art to reduce oily staining of polyester fabrics, are also useful in the detergent and laundry additive compositions of the present invention. U.S. Pat. No. 3,962,152 issued June 8, 1976, to Nicol et al., incorporated herein by reference, discloses copolymers of ethylene terephthalate and polyethylene oxide terephthalate as soil release agents. U.S. Pat. No. 4,174,305 issued Nov. 13, 1979, to Burns et al., incorporated herein by reference, discloses cellulose ether soil release agents. U.S. Ser. No. 684,511, filed Dec. 21, 1984, by Gosselink abandoned Jan. 16, 1986, incorporated herein by reference, discloses block polyester compounds useful as soil release agents in detergent and laundry additive compositions.

Especially preferred detergent compositions herein contain, in addition to a surfactant and the ether carboxylate mixture of this invention, a particular type of dispersant component. Such a dispersant component can contain the ethoxylated amine clay soil removal/anti-redeposition agents of the hereinbefore referenced European Patent Application No. EPA-112593 and/or acrylic acid polymers or acrylic/maleic acid copolymers. Such especially preferred detergent compositions are more completely described in the concurrently filed, copending U.S. Patent Application of Collins, Mackey and Spadini having Ser. No. 823910 filed Jan. 30, 1986.

The detergent and laundry additive compositions herein may also optionally contain one or more iron and magnesium chelating agents. Such chelating agents can be selected from the group consisting of amino carboxylates, amino phosphonates, polyfunctionally-substituted aromatic chelating agents and mixtures thereof, all as hereinafter defined. Without relying on theory, it is speculated that the benefit of these materials is due in part to their exceptional ability to remove iron and manganese ions from washing solutions by formation of soluble chelates.

Amino carboxylates useful as optional chelating agents in compositions of the invention have one or more, preferably at least two, units of the substructure

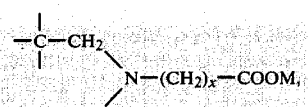

wherein M is hydrogen, alkali metal, ammonium or substituted ammonium (e.g. ethanolamine) and x is from 1 to about 3, preferably 1. Preferably, these amino carboxylates do not contain alkyl or alkenyl groups with more than about 6 carbon atoms. Alkylene groups can be shared by substructures. Operable amine carboxylates include ethylenediaminetetraacetates, N-hydroxyethylethylenediaminetriacetates, nitrilotriacetates, ethylenediamine tetrapropionates, diethylenetriaminepentaacetates, and ethanoldiglycines.

Amino phosphonates are also suitable for use as chelating agents in the compositions of the invention when at least low levels of total phosphorus are permitted in detergent compositions. Compounds with one or more, preferably at least two, units of the substructure

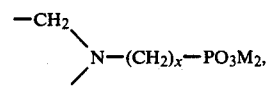

wherein M is hydrogen, alkali metal, ammonium or substituted ammonium and x is from 1 to about 3, preferably 1, are useful and include ethylenediaminetetrakis (methylenephosphonates), nitrilotris (methylenephosphonates) and diethylenetriaminepentakis (methylenephosphonates). Preferably, these amino phosphonates do not contain alkyl or alkenyl groups with more than about 6 carbon atoms. Alkylene groups can be shared by substructures.

Polyfunctionally-substituted aromatic chelating agents are also useful in the compositions herein. These materials comprise compounds having the general formula

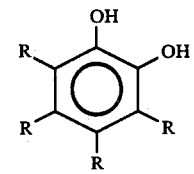

wherein at least one R is —SO$_3$H or —COOH or soluble salts thereof and mixtures thereof. U.S. Pat. No. 3,812,044 issued May 21, 1974, to Connor et al, incorporated herein by reference, discloses polyfunctionally-substituted aromatic chelating and sequestering agents. Preferred compounds of this type in acid form are dihydroxydisulfobenzenes and 1,2-dihydroxy -3,5-disulfobenzene or other disulfonated catechols in particular. Alkaline detergent compositions can contain these materials in the form of alkali metal, ammonium or substituted ammonium (e.g. mono-or triethanolamine) salts.

If utilized, optional chelating agents will generally comprise from about 0.1% to 10% by weight of the detergent or laundry additive compositions herein. More preferably chelating agents will comprise from about 0.75% to 3% by weight of such compositions.

The detergent and laundry additive compositions of this invention can also include a bleach system comprising an inorganic or organic peroxy bleaching agent and, in preferred compositions, an organic peroxy acid bleach precursor. Suitable inorganic peroxygen bleaches include sodium perborate mono- and tetrahydrate, sodium percarbonate, sodium persilicate and urea-hydrogen peroxide addition products and the clathrate $4Na_2SO_4 \cdot 2H_2O_2 \cdot 1NaCl$. Suitable organic bleaches include peroxylauric acid, peroxyoctanoic acid, peroxynonanoic acid, peroxydecanoic acid, diperoxydodecanedioic acid, diperoxyazelaic acid, mono- and diperoxyphthalic acid and mono- and diperoxyisophthalic acid. The bleaching agent is generally present in the detergent and laundry additive compositions of this invention at a level of from about 5% to about 50% preferably from about 10% to about 25% by weight.

The detergent and laundry additive compositions of the invention may also contain an organic peroxy acid bleach precursor at a level of from about 0.5% to about 10%, preferably from about 1% to about 6% by weight. Suitable bleach precursors are disclosed in UK-A-2040983, and include for example, the peracetic acid bleach precursors such as tetraacetylethylenediamine, tetraacetylmethylenediamine, tetraacetylhexylenediamine, sodium p-acetoxybenzene sulfonate, tetraacetylglycouril, pentaacetylglucose, octaacetyllactose, and methyl o-acetoxy benzoate. Highly preferred bleach precursors, however, have the general formula

wherein R is an alkyl group containing from 6 to 12 carbon atoms wherein the longest linear alkyl chain extending from and including the carboxyl carbon contains from 5 to 10 carbon atoms and L is a leaving group, the conjugate acid of which has a logarithmic acidity constant in the range from 6 to 13.

The alkyl group, R, can be either linear or branched and, in preferred embodiments, it contains from 7 to 9 carbon atoms. Preferred leaving groups L have a logarithmic acidity constant in the range from about 7 to about 11, more preferably from about 8 to about 10. Examples of leaving groups are those having the formula

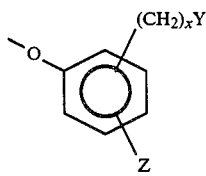 (a)

and

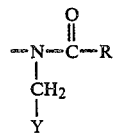 (b)

wherein Z is H, $R^1$ or halogen, $R^1$ is an alkyl group having from 1 to 4 carbon atoms, X is 0 or an integer of from 1 to 4 and Y is selected from $SO_3M$, $OSO_3M$, $CO_2M$, $N^+(R^1)_3O^-$ and $N^+(R^1)_2$—$O^-$ wherein M is H, alkali metal, alkaline earth metal, ammonium or substituted ammonium, and O is halide or methosulfate.

The preferred leaving group L has the formula (a) in which Z is H, x is 0 and Y is sulfonate, carboxylate or dimethylamine oxide radical. Highly preferred materials are sodium 3,5,5-trimethylhexanoyloxybenzene sulfonate, sodium 3,5,5-trimethylhexanoyloxybenzoate, sodium 2-ethylhexanoyl oxybenzenesulfonate, sodium nonanoyl oxybenzene sulfonate and sodium octanoyl oxybenzenesulfonate, the acyloxy group in each instance preferably being p-substituted.

The bleach precursor (activator) herein will normally be added in the form of particles comprising finely-divided bleach activator and a binder. The binder is generally selected from nonionic surfactants such as the ethoxylated tallow alcohols, polyethylene glycols, anionic surfactants, film forming polymers, fatty acids and mixtures thereof. Highly preferred are nonionic surfactant binders, the bleach activator being admixed with the binder and extruded in the form of elongated particles through a radial extruder as described in European Patent Application No. 62523. Alternatively, the bleach activator particles can be prepared by spray drying.

In addition to their utility as builders in detergent and laundry additive compositions, the ether carboxylates of the present invention may also be utilized in other contexts wherein water hardness sequestration is required. Thus, for example, the ether carboxylate compositions herein may be employed in water softening compositions, devices and methods. These materials are also useful in boiler descaling compositions and methods.

The following embodiments illustrate, but are not limiting of, the builder compounds and compositions of the present invention. All percentages herein are by weight unless indicated otherwise.

EXAMPLE I

In this example, a mixture of tartrate monosuccinate (TMS) and tartrate disuccinate (TDS) is prepared by a procedure which involves the reaction of maleate salts and tartrate salts. In such a procedure, maleic anhydride (2205 g, 22.5 moles) is heated in 2000 g of distilled water until dissolved. The resultant solution of maleic acid is cooled to 85±5° C. and 2250 g L-(+)-tartaric acid (15.0 moles) is added with stirring at 85±5° C. until a homogeneous clear acid solution is obtained.

Separately, 1111 g of calcium hydroxide (15.0 moles) is slowly added to a mixture of 4440 g of 50% sodium hydroxide solution (55.5 moles) and 1000 g distilled water while stirring at a moderate rate such that only a small fraction of unwetted calcium hydroxide is upon the surface of the solution at a time. Stirring is continued until an essentially uniform base mixture is obtained.

The base mixture is then added at a uniform rate over 0.5 hour to the moderately stirred acid solution which is at 70°–85° C. The resulting reaction mixture is cooled with warm (ca. 60° C.) water in order to maintain a reaction temperature of 90±5° C. most of the time. The reaction mixture may, however, boil briefly from time to time. The object is to prevent major losses of water vapor and also to limit the amount of insoluble salt which crystallizes upon the cool reaction vessel walls. As the last 10% of base is added, the reaction temperature is held at 85° C. The reaction mixture is quickly weighed and brought to 13,020 g, i.e., 50% active, with 200 g of distilled water. (Active is defined here as total weight of organics taken as their sodium salts i.e., sodium maleate and sodium tartrate or 160×22.5 moles + 194×15.0 moles = 6510 g.)

The reaction mixture is immediately heated with steam, stirred moderately in a covered reactor, and a 0.40 g sample taken with time arbitrarily set at zero. The reaction mixture which is a white suspension, is brought to 98°–100° C. within 10 minutes. Within 15 to 20 minutes of time zero, the reaction mixture clears. Samples (0.40±0.04 g) of the reaction solution are taken every half hour to be dissolved in 100 ml 0.1N sulfuric acid solution and immediately submitted for high pressure liquid chromatography (HPLC) analysis in order to monitor the course of the reaction.

The results of HPLC analysis of the 1.5 hour sample indicate that the reaction is to be quenched at the 2.0 hour point. Quenching consists of cooling the reaction product mixture to 50° C. within 10 minutes. The homogeneous, almost colorless quenched reaction product solution is reweighed and is made up again to 13,020 g with 327 g of distilled water to give a reaction product solution containing 50% active.

HPLC analysis indicates that the composition of the organic portion of the reaction product solution is 11.1% tartrate, 1.7% malate, 12.6% maleate, 10.9% fumarate, 35.0% peak 2A, 19.6% peak 2B, 3.3% peak 3A, and 5.9% peak 3B. Peaks 2A and 2B are isomers of sodium tartrate monosuccinate (TMS) and peaks 3A and 3B are isomers of sodium tartrate disuccinate (TDS). Therefore, the HPLC estimated yield of TMS+TDS based upon all peak areas is 63.7%. The approximate weight ratio of TMS:TDS is 86:14. All yields are based upon HPLC refractive index raw data, i.e., are not corrected to mole %. Calculated yield of this reaction based on tartrate is 4,139 g.

A second reaction product batch of the same size is made using similar procedures. HPLC analysis indicates that the composition of this second reaction product solution is 9.8% tartrate, 1.7% malate, 12.4% maleate, 10.1% fumarate, 35.0% peak 2A, 18.1% peak 2B, 5.1% peak 3A, and 7.9% peak 3B. Again peaks 2A and 2B are isomers of sodium tartrate monosuccinate (TMS) and peaks 3A and 3B are isomers of sodium tartrate disuccinate (TDS). Therefore, the HPLC-estimated yield of TMS+TDS based upon all peak areas is 66.1%. The approximate weight ratio of TMS:TDS is 80:20. Yield is 4400 g based on calculations.

Both reaction product batches are combined to give 26,040 g of solution which is calculated to contain 8539 g of TMS/TDS and 30 moles of calcium ion. This solution is then diluted with 26,040 g of water. While this solution is at 26° C. and stirred vigorously, a 28% solution of 7500 g (30 mole) of ethanehydroxydiphosphonate disodium salt dissolved in 18,750 g of water is added followed by 3178 g of 50% sodium hydroxide solution to give a pH of 10.5. Stirring is continued for 18 hours; the final pH is eleven. The resulting precipitate (EHDP-calcium complex) is then removed by filtration using suction filtration equipment with a paper filter, and the filtrate is washed with 4 liters of water. The resulting supernatant, 56 liters, is filtered again through a glass frit to remove any remaining fine particles. This clear solution is then evaporated in a steam heated vat with a compressed air stream blown above the surface to give a solution of 32,550 g.

This solution is then poured into 80 liters of vigorously stirred methanol. This is done to help separate the less soluble TMS and TDS from the more soluble maleic and fumaric acid salts. The stirring is continued for 15 minutes followed by a ½ hour settling period. Then the liquid is decanted from the gummy solid by siphon. This solid is dissolved in 13,500 g of distilled water to give 26,685 g of solution which is then poured into 68 liters of methanol, essentially repeating the above. The resulting solid is dissolved in 6 liters of distilled water (pH = 8.4), and the vat is heated with steam. Methanol is removed with a stream of nitrogen directed on the surface of the solution which is well stirred. This is continued until 'H-NMR analysis indicates that the methanol is removed. The resulting solution is 16,380 g. To reduce viscosity, 2 liters of water are added, and the mixture is filtered to give 18,887 g of solution. This solution is analyzed and found to have the following composition by high pressure liquid chromatography using a refractive index detector: 43.6% TMS/TDS (8,235 g or 96.4% recovery by workup), 2.1% tartrate, 0.5% malate, 0.9% maleate, and 1.1% fumarate. The TMS/TDS ratio is 78.2:21.8. The calcium ion level of the solution is 0.048 weight % as determined by atomic absorption.

EXAMPLE II

A TMS/TDS reaction product mixture is prepared using procedures similar to those set forth in Example I except that the reactants used to form the reaction mixture are maleic anhydride, tartaric acid, sodium hydroxide and calcium hydroxide in a 1.3:1.0:3.93:0.5 molar ratio. The resulting reaction product mixture is determined by high pressure liquid chromatography to contain 17.2% tartrate, 1.5% malate, 9.9% maleate, 10.3% fumarate, TMS (2A 36.2%, 2B 13.4%) and TDS (3A 5.3%, 3B 6.1%). The rest of the sample is a mixture of water and calcium salts.

Calcium is then removed from this mixture by a precipitation procedure using a combination of carbonate salts. In such a procedure 26.5 grams of sodium carbonate and 21.0 grams of sodium bicarbonate (0.25 mole of each salt) are dissolved in 204 grams of water. This solution is then added to 250 grams of the above-described reaction product mixture which contains 0.125 moles of calcium. The resulting mixture is placed in a 1 liter flask equipped with a thermometer and stirrer. This mixture is then heated to 70° C. and stirred for 3 hours. After cooling to 25° C. while stirring is continued, this mixture is filtered through a sintered glass filter. The resulting filter cake is washed with 20 ml of water twice. The filtrate is adjusted to a weight of 1000 grams with the addition of water and then is analyzed. The filtrate is found to contain tartrate—1.48%; malate—0.14%; maleate—1.02%; fumarate—0.83%; TMS—(2A 3.3%, 2B 1.3%); TDS—(3A 0.5%, 3B 0.5%); and calcium—0.009%. The maleate and fumarate salts are then removed using a methanol precipitation procedure as in Example I.

EXAMPLE III

Another TMS/TDS reaction product mixture is prepared by reacting tartaric acid and maleic anhydride. In this preparation 150 g (1 mole) of L-tartaric acid are placed in 86.5 g. of water, and this mixture is heated to give a solution. Then while this solution is cooled and stirred vigorously, a slurry of 224 g. (2.8 moles) of sodium hydroxide (50% solution in water) and 74.0 g. (1.0 mole) of calcium hydroxide are added. The resulting milky mixture is stirred and cooled to maintain a temperature of about 75° C. while 98.0 g. (1.0 mole) of maleic anhydride are added. This results in a slightly yellow solution.

This reaction mixture is then stirred and maintained at 75° C. for 20.5 hours. During the reaction very small samples are removed and analyzed by HPLC. The following distributions of reaction products are determined in the samples tested:

| Product Compounds | Reaction Time hours | |
|---|---|---|
| | 6.5 | 20.5 |
| Tartaric acid | 12.7% | 8.2% |
| Malic acid | — | 0.7 |
| Maleic acid | 10.1 | 3.4 |
| Fumaric acid | 1.2 | 3.6 |
| TMS (2A) | 37.6 | 40.3 |
| TMS (2B) | 11.1 | 12.1 |
| TDS (3A) | 16.5 | 18.5 |
| TDS (3B) | 10.8 | 13.2 |
| Total builder | 76.0% | 84.1% |

Using the procedures described in Example II, calcium is removed from this reaction product to a level such that the ratio of moles of calcium to the total mole of TMS+TDS is less than 1:10.

EXAMPLE IV

Various mixtures of sodium tartrate monosuccinate (TMS) and sodium tartrate disuccinate (TDS) are prepared in accordance with the procedure of Example I. In this procedure, various molar ratios of maleate and tartrate reactants are employed to give ether carboxylate reaction products having a variety of TMS/TDS ratios. Reactant ratios, product compositions and percent conversion of reactants to TMS/TDS product are set forth in Table I.

TABLE I

| Maleate/Tartrate Ratio of Equivalents | TMS in Product (Wt %) | TDS in Product (Wt %) | Conversion of Reactants to Product (%) |
|---|---|---|---|
| 8.0 | 21 | 79 | 33 |
| 4.0 | 46 | 54 | 48 |
| 2.5 | 44 | 56 | 65 |
| 2.0 | 50 | 50 | 71 |
| 1.5 | 58 | 42 | 79 |
| 1.25 | 82 | 18 | 71 |
| 1.0 | 82 | 18 | 70 |
| 0.83 | 82 | 18 | 69 |
| 0.67 | 89 | 11 | 58 |
| 0.50 | 97 | 3 | 34 |

The Table I data illustrate that product mixtures containing various TMS/TDS ratios can be prepared by adjusting the relative amounts of maleate and tartrate starting materials. The Table I data further illustrate that maximum conversion of reactants to desired products is achieved for the reactions wherein the maleate/tartrate ratio varies between about 2.5:1 and 0.80:1.

EXAMPLE V

In this example, calcium sequestering performance of various builder materials, including a TMS/TDS-containing mixture of the present invention, is measured using a Divalent Electrode titration procedure. Such a procedure is described in general in Matzner et al; "Organic Builder Salts (I)," *Tenside Detergents*, Vol. 10, 1973 Heft 3 at pages 123–124, incorporated herein by reference.

In accordance with such procedures, a $1.2 \times 10^{-3}$M calcium chloride solution (25 ml; 0.1M buffer; 35° C.; pH-9.55) is titrated on an automatic titrator using a 1% solution of the sodium salt of various sequestering builder materials. Uncomplexed calcium ion concentration is detected by the change in millivolt potential of a calcium selective electrode as a function of millimoles of builder added.

Builder materials tested include a TMS/TDS mixture in a 78:22 weight ratio, sodium oxydisuccinate (ODS), sodium carboxymethyloxysuccinate (CMOS), sodium oxydiacetate (ODA) and sodium tripolyphosphate (STP). Test results are depicted graphically in the FIGURE wherein the molar amount of builder added is plotted along the X-axis and the change in potential at the calcium selective electrode provided by titrating the various builder solutions is plotted along the Y-axis. The proximity of any given resulting curve to the Y-axis indicates the effectiveness with which the builder acts to sequester free calcium ion. The proximity of any such curve to the X-axis indicates an enhanced ability of the builder to keep calcium ion concentration to low levels in the solution.

The curves set forth in the FIGURE indicate that the TMS/TDS mixtures of the present invention provide superior calcium sequestration performance in comparison with other ether carboxylates such as oxydisuccinate, oxydiacetate and carboxymethyloxysuccinate and even in comparison with the phosphate builder, sodium tripolyphosphate.

EXAMPLE VI

A granular detergent composition for household laundry use is as follows:

| Component | Wt. % |
|---|---|
| Sodium $C_{14}$—$C_{15}$ alkylsulfate | 13.3 |
| Sodium $C_{13}$ linear alkyl benzene sulfonate | 5.7 |
| $C_{12}$—$C_{13}$ alkylpolyethoxylate (6.5) | 1.0 |
| Sodium toluene sulfonate | 1.0 |
| TMS/TDS, sodium salt, 86/14 weight ratio of TMS:TDS of the Example I type | 25.0 |
| Sodium N—hydroxyethylethylenediaminetriacetate | 2.0 |
| Sodium polyacrylate (Avg. M.W. approx. 5000) | 2.0 |
| Sodium carbonate | 20.3 |
| Sodium silicate | 5.8 |
| Polyethylene glycol (Avg. M.W. approx. 8000) | 1.0 |
| Sodium sulfate, water and miscellaneous | Balance to 100% |

The components are added together with continuous mixing with sufficient extra water (about 40% total) to form an aqueous slurry which is then spray dried to form the composition.

In the composition of Example I the following substitution can be made:
(a) for TMS/TDS:
(1) an equivalent amount of TMS alone, and
(2) an equivalent amount of TDS alone.

EXAMPLE VII

A liquid detergent composition for household laundry use is as follows:

| Component | Wt. % |
|---|---|
| Potassium $C_{14}$—$C_{15}$ alkyl polyethoxy (2.5) sulfate | 8.3 |
| $C_{12}$—$C_{14}$ alkyl dimethyl amine oxide | 3.3 |
| Potassium toluene sulfonate | 5.0 |

-continued

| Component | Wt. % |
|---|---|
| Monoethanolamine | 2.3 |
| TMS/TDS triethanolamine salt, 85/15 TMS/TDS | 15.0 |
| Potassium salt of 1,2-dihydroxy-3,5-disulfobenzene | 1.5 |
| Potassium polyacrylate (avg. M.W. approx. 9000) | 1.5 |
| Water and miscellaneous | Balance to 100% |

The components are added together with continuous mixing to form the composition.

EXAMPLE VIII

A liquid detergent composition for household laundry use is prepared by mixing the following ingredients:

| | |
|---|---|
| $C_{13}$ alkylbenzenesulfonic acid | 10.5% |
| Triethanolamine cocoalkyl sulfate | 4.0 |
| $C_{14-15}$ alcohol ethoxy-7 | 12.0 |
| $C_{12-18}$ alkyl monocarboxylic acids | 15.0 |
| TMS/TDS, triethanolamine salt 85/15 TMS/TDS | 5.0 |
| Diethylenetriaminepentakis (methylenephosphonic) acid | 0.8 |
| Polyacrylic acid (avg. M.W. approx. 5000) | 0.8 |
| Triethanolamine | 4.5 |
| Ethanol | 8.6 |
| 1,2-Propanediol | 3.0 |
| Water, perfume, buffers and miscellaneous | Balance to 100% |

EXAMPLE IX

In the Compositions which follow, the abbreviations used have the following designations:

| | |
|---|---|
| $C_{12}LAS$ | Sodium linear $C_{12}$ benzene sulfonate |
| TAS | Sodium tallow alcohol sulfonate |
| $TAE_n$ | Hardened tallow alcohol ethoxylated with n moles of ethylene oxide per mole of alcohol |
| Dobanol $45_E7$ | A $C_{14-15}$ primary alcohol condensed with 7 moles of ethylene oxide |
| TAED | Tetraacetyl ethylene diamine |
| NOBS | Sodium nonanoyl oxybenzenesulfonate |
| INOBS | Sodium 3,5,5 trimethyl hexanoyl oxybenzene sulfonate |
| Silicate | Sodium silicate having an $SiO_2:Na_2O$ ratio of 1:6 |
| Sulfate | Anhydrous sodium sulfate |
| Carbonate | Anhydrous sodium carbonate |
| CMC | Sodium carboxymethyl cellulose |
| Silicone | Comprising 0.14 parts by weight of an 85:15 by weight mixture of silanated silica and silicone, granulated with 1.3 parts of sodium tripolyphosphate, and 0.56 parts of tallow alcohol condensed with 25 molar proportions of ethylene oxide |
| PC1 | Copolymer of 3:7 maleic/acrylic acid, average molecular weight about 70,000, as sodium salt |
| PC2 | Polyacrylic acid, average molecular weight about 4,500, as sodium salt |
| TMS/TDS | Mixture of tartrate monosuccinate and tartrate disuccinate in an TMS to TDS weight ratio of 85/15 sodium salt form |
| Perborate | Sodium perborate tetrahydrate of nominal formula $NaBO_2.3H_2O.H_2O_2$ |
| Enzyme | Protease |
| EDTA | Sodium ethylene diamine tetra acetate |
| Brightener | Disodium 4,4'-bis(2-morpholino-4-anilino-s-triazin-6-ylamino) stilbene-2:2'-disulfonate |
| DETPMP | Diethylene triamine penta(methylene phosphonic acid), marketed by Monsanto under the Trade name Dequest 2060 |
| EDTMP | Ethylenediamine tetra (methylene phosphonic acid), marketed by Monsanto, under the Trade name Dequest 2041 |

Granular detergent compositions are prepared as follows. A base powder composition is first prepared by mixing all components except, where present, Dobanol 45E7, bleach, bleach activator, enzyme, suds suppresser, phosphate and carbonate in crutcher as an aqueous slurry at a temperature of about 55° C. and containing about 35% water. The slurry is then spray dried at a gas inlet temperature of about 330° C. to form base powder granules. The bleach activator, where present, is then admixed with $TAE_{25}$ as binder and extruded in the form of elongated particles through a radical extruder as described in European Patent Application No. 62523. The bleach activator noodles, bleach, enzyme, suds suppressor, phosphate and carbonate are then dry-mixed with the base powder composition and finally Dobanol 45E7 is sprayed into the final mixture.

| | COMPOSITIONS | | | |
|---|---|---|---|---|
| | A | B | C | D |
| $C_{12}LAS$ | 4 | 9 | 8 | 8 |
| TAS | 4 | 3 | — | 3 |
| $TAE_{25}$ | 0.5 | 0.5 | 0.8 | — |
| $TAE_{11}$ | — | 1 | — | — |
| Dobanol 45E7 | 4 | — | 4 | 2 |
| NOBS | — | 2 | — | — |
| INOBS | 3 | — | — | — |
| TAED | 0.5 | — | 3 | — |
| Perborate | 19 | 20 | 10 | 24 |
| EDTMP | 0.3 | — | 0.4 | 0.1 |
| DETPMP | — | 0.4 | — | — |
| EDTA | 0.2 | 0.2 | 0.2 | 0.1 |
| Magnesium (ppm) | 1000 | 1000 | 750 | — |
| PC1 | 2 | 1 | 2 | 2 |
| PC2 | 1 | 1 | — | 1 |
| TMS/TDS | 25 | 7 | 15 | 10 |
| Zeolite A* | — | 15 | 14 | — |
| Sodium tripolyphosphate | — | — | — | 12 |
| Coconut Soap | — | — | — | 2 |
| Carbonate | 17 | 15 | 10 | — |
| Silicate | 3 | 2 | 2 | 7 |
| Silicone | 0.2 | 0.2 | 0.3 | 0.2 |
| Enzyme | 0.8 | 0.5 | 0.4 | 0.3 |
| Brightener | 0.2 | 0.2 | 0.2 | 0.2 |
| Sulfate, Moisture & Miscellaneous | to 100 | | | |

*Zeolite A of 4 A pore size.

The above compositions are zero and low phosphate detergent compositions displaying excellent bleach stability, fabric care and detergency performance across the range of wash temperatures with particularly outstanding performance in the case of Compositions A, B and C on greasy and particulate soils at low wash temperatures.

EXAMPLE X

A liquid detergent composition suitable for use in cleaning hard surfaces is prepared having the following composition:

| Component | Wt. % |
|---|---|
| $C_{13}$ alkylbenzene sulfonic acid | 5% |
| TMS/TDS, sodium salt 80:20 TMS/TDS | 9% |
| Sodium Carbonate | 2% |

| Component | Wt. % |
|---|---|
| Isopropyl Alcohol | 3% |
| Pine Oil | 6% |
| Water, Fragrance, Miscellaneous | Balance to 100% |

What is claimed is:

1. An ether carboxylate composition suitable for use as a builder in detergent formulations, said composition comprising
   (a) from about 1% to 99% by weight of a tartrate monosuccinate component of the structure:

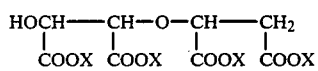

wherein X is H or a salt-forming cation; and
   (b) from about 1% to 99% by weight of a tartrate disuccinate component of the structure:

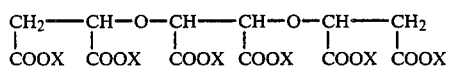

wherein X is H or a salt-forming cation.

2. A composition according to claim 1 wherein the weight ratio of tartrate monosuccinate component to tartrate disuccinate component ranges from about 97:3 to 20:80.

3. A composition according to claim 2 wherein the tartrate monosuccinate and the tartrate disuccinate components are in the form of their fully neutralized sodium, potassium, monoethanolamine or triethanolamine salts.

4. A composition according to claim 3 wherein the tartrate monosuccinate component comprises from about 10% to 98% by weight of the composition; wherein the tartrate disuccinate component comprises from about 2% to 90% by weight of the composition; and wherein the weight ratio of tartrate monosuccinate to tartrate disuccinate ranges from about 95:5 to 40:60.

5. A composition according to claim 3 wherein the composition contains up to about 70% by weight of an additional component selected from the group consisting of water, malate salts, maleate salts, tartrate salts, fumarate salts, calcium salts, and combinations of said optional components.

6. A composition according to claim 5 wherein the composition contains no more than about 10 mole percent of calcium based upon total moles of the tartrate monosuccinate and tartrate disuccinate present in said composition.

7. A composition according to claim 6 wherein the weight ratio of tartrate monosuccinate to tartrate disuccinate ranges from about 95:5 to 40:60.

8. A tartrate monosuccinic acid, or a salt thereof, of the structure:

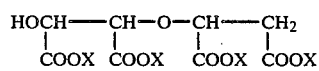

wherein X is H or a salt-forming cation.

9. Tartrate disuccinic acid, or a salt thereof, of the structure:

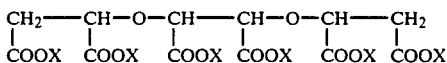

wherein X is H or a salt-forming cation.

10. A process for preparing a combination of ether carboxylates useful as a detergent builder, which method comprises
   (a) forming an aqueous reaction mixture comprising from about 20% to 60% by weight of both calcium and monovalent cation salts of maleic acid and tartaric acid, said mixture corresponding to the overneutralized mixture which is formed by combining:
      (i) maleic and tartaric acids in a maleic to tartaric molar ratio of from about 0.5:1 to about 8:1;
      (ii) a source of calcium cations in an amount such that the molar ratio of calcium to tartaric acid ranges from about 0.1:1 to 2.0:1 with the ratio of moles of calcium to total moles of maleic and tartaric acid being less than 1; and
      (iii) a neutralizing agent comprising an hydroxide of a monovalent cation in an amount such that the ratio of moles of monovalent cation to moles of maleic acid plus moles of tartaric acid minus moles of calcium ranges from about 2.1:1 to 3.8:1 and
   (b) maintaining said aqueous reaction mixture at a temperature of from about 20° C. to 120° C. for a time period sufficient to form a reaction product mixture of
      (i) tartrate monosuccinate of the fomula:

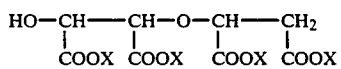

wherein X is a salt-forming cation; and
      (ii) tartrate disuccinate of the formula:

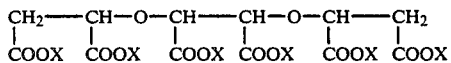

wherein X is a salt-forming cation; and
   (c) reducing the calcium content of said reaction product mixture to the extent that the molar ratio of calcium to the tartrate succinate reaction products is less than about 1:10.

11. A process according to claim 10 wherein the reaction mixture comprises from about 40% to 55% by weight of said salts of maleic and tartaric acids.

12. A process according to claim 11 wherein
   (a) the maleic acid salt is selected from sodium and potassium maleate;
   (b) the tartaric acid salt is selected from sodium and potassium tartrate; and
   (c) the calcium cations are provided by calcium hydroxide; and
   (d) the monovalent cation-containing neutralizing agent is selected from sodium hydroxide, potassium hydroxide and ammonium hydroxide.

13. A process according to claim 12 wherein the maleic acid salt and tartaric acid salt reactants are formed in the reaction mixture in situ.

14. A process according to claim 12 wherein
   (a) the molar ratio of maleic acid to tartaric acid used in forming the reaction mixture ranges from about 0.9:1 to 1.2:1 and (b) the molar ratio of calcium cations to tartaric acid used in forming the reaction mixture ranges from about 0.8:1 to 1.5:1.

15. A process according to claim 12 wherein the molar ratio of calcium to tartrate succinate reaction products is reduced to less than about 1:20 by addition to the reaction mixture of a precipitating agent selected from alkali metal carbonate, alkali metal bicarbonate and mixtures thereof.

16. A process according to claim 12 wherein the aqueous reaction mixture is maintained at a temperature of from about 50° C. to 80° C. for a period of from about 0.5 to 10 hours.

17. A detergent composition comprising from about 0.5% to 98% by weight of a surfactant and from about 2% to 99.5% by weight of a builder component selected from the group consisting of
(a) tartrate monosuccinic acid, or salt thereof, of the structure

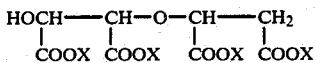

wherein X is H or a salt-forming cation;
(b) tartrate disuccinic acid, or salt thereof, of the structure:

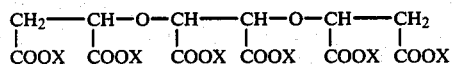

wherein X is H or a salt-forming cation, or
(c) a combination of said tartrate monosuccinic acid or salt and said tartrate disuccinic acid or salt, in a weight ratio of tartrate monosuccinic acid or salt, to tartrate disuccinic acid or salt, of from about 97:3 to 20:80.

18. A detergent composition according to claim 17 which contains from about 5% to 95% by weight of an additional component selected from the group consisting of additional detergent builders, chelating agents, enzymes, fabric whiteners and brighteners, sudsing control agents, solvents, hydrotropes, bleaching agents, bleach precursors, buffering agents, soil removal/anti-redeposition agents, soil release agents, fabric softening agents, perfumes, solvents, opacifiers and combinations of said additional components.

19. A laundry additive composition comprising
(A) from about 2% to 99.5% by weight of a builder component selected from the group consisting of
(i) tartrate monosuccinic acid, or salt thereof, of the structure

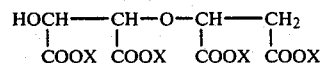

wherein X is H or a salt-forming cation;
(ii) tartrate disuccinic acid, or salt thereof, of the structure:

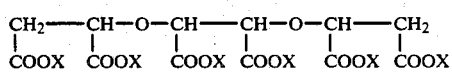

wherein X is H or a salt-forming cation, or
(iii) a combination of said tartrate monosuccinic acid or salt and said tartrate disuccinic acid or salt, in a weight ratio of tartrate monosuccinic acid or salt, to tartrate disuccinic acid or salt, of from about 97:3 to 20:80; and
(B) from about 0.5% to 98% by weight of a laundry adjuvant selected from the group consisting of surfactants, additional detergent builders, chelating agents, enzymes, fabric whiteners and brighteners, sudsing control agents, solvents, hydrotropes, bleaching agents, bleach precursors, buffering agents, soil removal/anti-redeposition agents, soil release agents, fabric softening agents, perfumes, colorants, opacifiers and combinations of said laundry adjuvants.

20. A laundry additive composition according to claim 19 wherein
(A) the builder component comprises a combination of sodium tartrate monosuccinate and sodium tartrate disuccinate; and
(B) the laundry adjuvant is selected from surfactants, bleaching agents, bleach precursors, enzymes and combinations of said laundry adjuvants.

* * * * *

REEXAMINATION CERTIFICATE (1673rd)

United States Patent [19]
Bush et al.

[11] B1 4,663,071
[45] Certificate Issued Apr. 7, 1992

[54] ETHER CARBOXYLATE DETERGENT BUILDERS AND PROCESS FOR THEIR PREPARATION

[75] Inventors: Rodney D. Bush; Daniel S. Connor; Stephen W. Heinzman, all of Cincinnati; Larry N. Mackey, Fairfield, all of Ohio

[73] Assignee: The Procter & Gamble Company, Cincinnati, Ohio

Reexamination Request:
No. 90/002,092, Jul. 20, 1990

Reexamination Certificate for:
Patent No.: 4,663,071
Issued: May 5, 1987
Appl. No.: 823,909
Filed: Jan. 30, 1986

[51] Int. Cl.$^5$ .............. C11D 17/00; C11D 3/20; C11D 7/26
[52] U.S. Cl. .............. 252/174.19; 252/142; 252/DIG. 11
[58] Field of Search ........... 252/142, 174.19, DIG. 11

[56] References Cited
U.S. PATENT DOCUMENTS
4,125,485  11/1978  Lannert .................. 252/546

FOREIGN PATENT DOCUMENTS
707910  11/1970  South Africa .

OTHER PUBLICATIONS
"Nitrogen- and Phosphorus-Free Strong Sequestering Builders", Tenside Detergents, No. 12, 1974, pp. 47-51, H. C. Kemper, et al.
"Microbial Degradation of Surfactants and 'Builder' Components", FEMS Symposium No. 12, Academic Press, 1981, pp. 325-369, T. Leisinger, et al.

*Primary Examiner*—A. Lionel Clingman

[57] ABSTRACT

Provided herein are ether carboxylate builder compositions comprising a combination of tartrate monosuccinic acid (or salts thereof) and tartrate disuccinic acid (or salts thereof). Such mixtures can be prepared by reacting water-soluble, mixed maleic acid salts with mixed tartaric acid salts. Both components of the resulting ether carboxylate mixture act as sequestering agents and are useful as detergency builders. Detergent and laundry additive compositions incorporating these ether carboxylates can be prepared without use of detergent builder components containing phosphorus or nitrogen.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 9-16 is confirmed.

Claims 4, 7, and 8 are cancelled.

Claims 1-2, 17 and 19 are determined to be patentable as amended.

Claims 3, 5-6, 18 and 20, dependent on an amended claim, are determined to be patentable.

New claims 21-27 are added and determined to be patentable.

1. An ether carboxylate composition suitable for use as a builder in detergent formulations, said composition [comprising] *consisting essentially of*
   (a) from about [1% to 99%] *20% to 97%* by weight of a tartrate monosuccinate component of the structure:

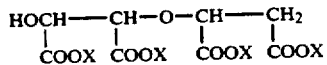

wherein X is H or a salt-forming cation; and
   (b) from about [1% to 99%] *3% to 80%* by weight of a tartrate disuccinate component of the structure:

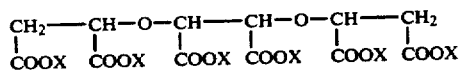

wherein X is H or a salt-forming cation; *the weight ratio of the tartrate monosuccinate component to the tartrate disuccinate component ranging from about 89:11 to 44:56.*

2. A composition according claim 1 wherein the weight ratio of tartrate monosuccinate component to tartrate disuccinate component ranges from about [97:3 to 20:80] *82:18 to 50:50.*

17. A detergent composition comprising from about 0.5% to 98% by weight of a surfactant and from about 2% to 99.5% by weight of a builder component [selected from the group] consisting *essentially* of
   (a) tartrate monosuccinic acid, or salt thereof, of the structure

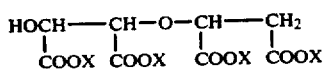

wherein X is H or a salt-forming cation; *and*
   (b) tartrate disuccinic acid, or salt thereof, of the structure;

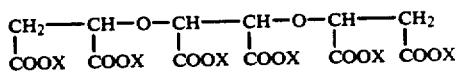

wherein X is H or a salt-forming cation, [or
   (c) a combination of said tartrate monosuccinic acid or salt and said tartrate disuccinic acid or salt,] in a weight ratio of tartrate monosuccinic acid or salt, to tartrate disucinnic acid or salt, of from about [97:3 to 20:80] *89:11 to 44:56.*

19. A laundry additive composition comprising
   (A) from about 2% to 99.5% by weight of a builder component [selected from the group] consisting *essentially* of
      (i) tartrate monosuccinic acid, or salt thereof, of the structure

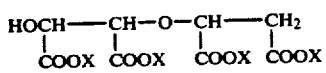

wherein X is H or a salt-forming cation; *and*
      (ii) tartrate disuccinic acid, or salt thereof, of the structure

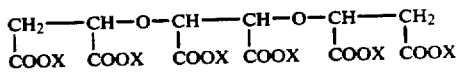

wherein X is H or a salt-forming cation; [or
      (iii) a combination of said tartrate monosuccinic acid or salt and said tartrate disuccinic acid or salt,] in a weight ratio of tartrate monosuccinic acid or salt, to tartrate disuccinate acid or salt, of from about [97:3 to 20:80] *89:11 to 44:56*; and
   (B) from about 0.5% to 98% by weight of a laundry adjuvant selected from the group consisting of surfactants, additional detergent builders, chelating agents, enzymes, fabric whiteners and brighteners, sudsing control agents, solvents, hydrotropes, bleaching agents, bleach precursors, buffering agents, soil removal/anti-redeposition agents, soil release agents, fabric softening agents, perfumes, colorants, opacifiers and combinations of said laundry adjuvants.

21. *A process for preparing a combination of ether carboxylates useful as a detergent builder, which method comprises*
   (a) *forming an aqueous reaction mixture from about 40% to 60% by weight of both calcium and monovalent cation salts of maleic acid and tartaric acid, said mixture corresponding to the overneutralized mixture which is formed by combining:*
      (i) *maleic and tartaric acids in a maleic to tartaric molar ratio of from about 0.5:1 to about 8:1;*
      (ii) *a source of calcium cations in an amount such that the molar ratio of calcium to tartaric acid ranges from about 0.5:1 to 2.0:1 with the ratio of moles of calcium to total moles of maleic and tartaric acid being less than 1; and*
      (iii) *a neutralizing agent comprising an hydroxide of a monovalent cation in an amount such that the ratio of moles of monovalent cation to moles of maleic acid plus moles of tartaric acid minus moles of calcium ranges from about 2.1:1 to 3.8:1 and*

(b) maintaining said aqueous reaction mixture at a temperature of from about 20° C. to 120° C. for a time period sufficient to form a reaction product mixture of (i) tartrate monosuccinate of the formula:

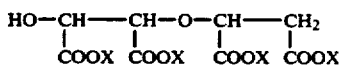

wherein X is a salt-forming cation; and (ii) tartrate disuccinate of the formula:

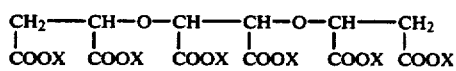

wherein X is a salt-forming cation; and (c) reducing the calcium content of said reaction product mixture to the extent that the molar ratio of calcium to the tartrate succinate reaction products is less than about 1:10.

22. A process according to claim 1 wherein the reaction mixture comprises from about 40% to 55% by weight of said salts of maleic and tartaric acids.

23. A process according to claim 22 wherein (a) the maleic acid salt is selected from sodium and potassium maleate;

(b) the tartaric acid salt is selected from sodium and potassium tartrate; and (c) the calcium cations are provided by calcium hydroxide; and (d) the monovalent cation-comprising neutralizing agent is selected from sodium hydroxide, potassium hydroxide and ammonium hydroxide.

24. A process according to claim 23 wherein the maleic acid salt and tartaric acid salt reactants are formed in the reaction mixture in situ.

25. A process according to claim 23 wherein (a) the molar ratio of maleic acid to tartaric acid used in forming the reaction mixture of ranges from about 0.9:1 to 1.2:1 and (b) the molar ratio of calcium cations to tartaric acid used in forming the reaction mixture ranges from about 0.8:1 to 1.5:1.

26. A process according to claim 23 wherein the molar ratio of calcium to tartrate succinate reaction products is reduced to less than about 1:20 by addition the reaction mixture of a precipitating agent selected from alkali metal carbonate, alkali metal bicarbonate and mixtures thereof.

27. A process according to claim 23 wherein the aqueous reaction mixture is maintained at a temperature of from about 50° C. to 80° C. for a period of from about 0.5 to 10 hours.

* * * * *